(12) United States Patent
Nielsen et al.

(10) Patent No.: US 8,481,561 B2
(45) Date of Patent: Jul. 9, 2013

(54) CLASSES OF GABAA/BZR LIGANDS

(75) Inventors: Mogens Peter Cherly Nielsen, Roskilde (DK); Tommy Liljefors, Frederiksberg (DK); Jakob Alexander Nilsson, Lund (SE); Olov A Sterner, Malmö (SE)

(73) Assignee: Innovationspatent Sverige AB, Lund (SE)

( * ) Notice: Subject to any disclaimer, the term of this patent is extended or adjusted under 35 U.S.C. 154(b) by 151 days.

(21) Appl. No.: 12/936,045

(22) PCT Filed: Apr. 2, 2009

(86) PCT No.: PCT/SE2009/000175
§ 371 (c)(1),
(2), (4) Date: Dec. 13, 2010

(87) PCT Pub. No.: WO2009/123536
PCT Pub. Date: Oct. 8, 2009

(65) Prior Publication Data
US 2011/0105553 A1      May 5, 2011

(30) Foreign Application Priority Data
Apr. 4, 2008  (SE) ....................................... 0800758

(51) Int. Cl.
*A61K 31/4365* (2006.01)
*C07D 471/04* (2006.01)

(52) U.S. Cl.
USPC ................................ 514/291; 546/83; 546/84

(58) Field of Classification Search
USPC ........................................ 546/83, 84; 514/291
See application file for complete search history.

(56) References Cited

U.S. PATENT DOCUMENTS
5,182,290 A    1/1993  Albaugh
6,268,496 B1   7/2001  Shaw

OTHER PUBLICATIONS

Erik Lager, et al; "4-Quinolone Derivatives: High-Affinity Ligands at the Benzodiazepine Site of Brain GABA$_A$ Receptors, Synthesis, Pharmacology, and Pharmacophore Modeling", J. Med. Chem. 2006, vol. 49, pp. 2526-2533, table 1.
Povl Krogsgaard-Larsen, et al; "GABA$_A$ agonists and partial agonists: THIP (Gaboxadol) as a non-opiod analgesic and a novel type of hypnotic", Biochemical Pharmacology 2004, vol. 68, pp. 1573-1580, figures 1-5, abstract.
Vittoria Colotta, et al; "Tricyclic Heteroaromatic System. [1]Benzopyranopyrrol-4-ones and [1]BEnzopyrano-1,2,3-triazol-4-ones as Benzodiazepine Receptor Ligands. Synthesis and Structure-Activity Relationships", J. Med. Chem. 1990, vol. 33, No. 9, pp. 2646-2651, compounds A-F.
International Search Report: PCT/SE2009/000175, Jun. 29, 2009.
European Search Report; dated Oct. 19, 2011; EP 09 72 7437.
International Preliminary Report on Patentability mailed Oct. 14, 2010; PCT/SE2009/000175.

*Primary Examiner* — Rita Desai
(74) *Attorney, Agent, or Firm* — Ladas & Parry LLP

(57) ABSTRACT

The present invention relates to novel GABA$_A$/BzR ligands of the general formulas (I), (II) and (III) wherein R$_1$ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and R$_2$ is selected from the group consisting of hydrogen, halogen and alkyl having 1 to 2 carbon atoms, as well as the use of these compounds for treating anxiolytic, anticonvulsant, sedative-hypnotic and myorelaxant conditions as well as anxiogenic, somnolytic and convulsant conditions in mammals including pharmaceutical compositions comprising the same.

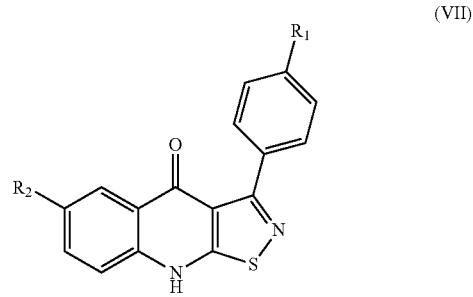

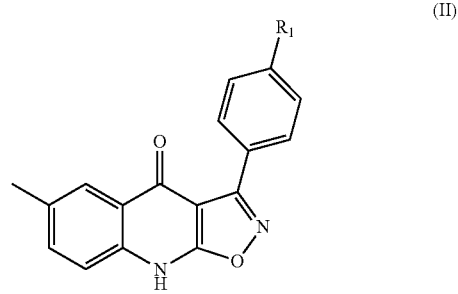

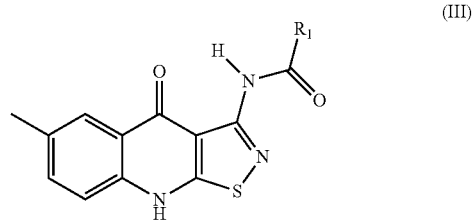

14 Claims, 1 Drawing Sheet

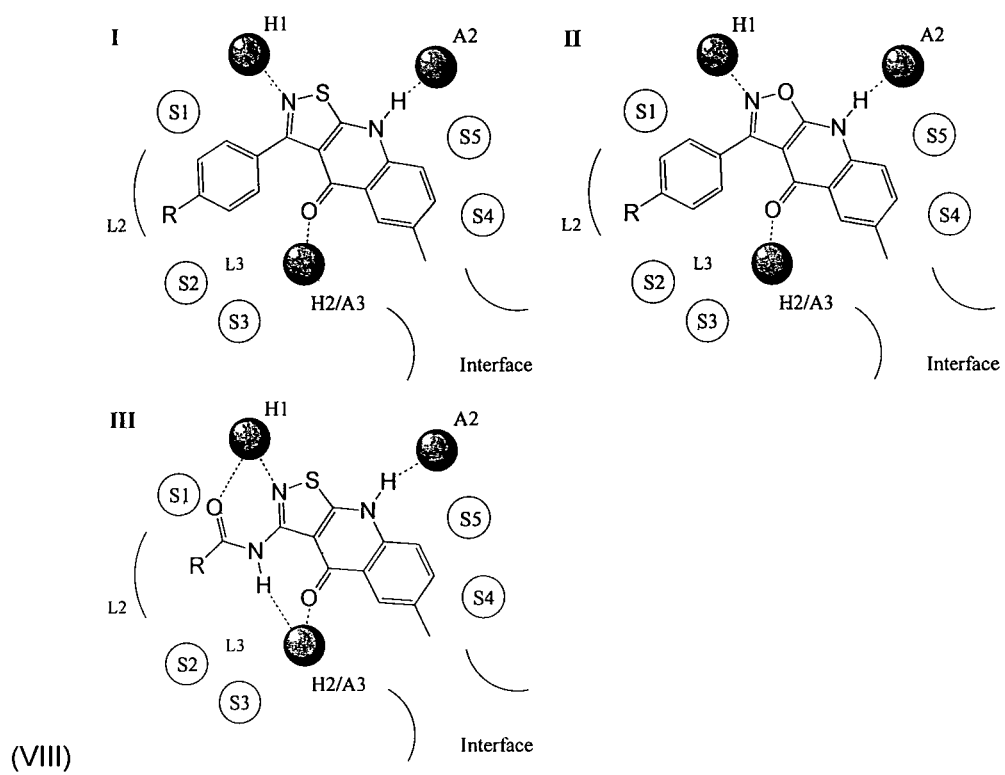
(VIII)

CLASSES OF GABAA/BZR LIGANDS

TECHNICAL FIELD

The present invention relates to a new class of $GABA_A$/BzR ligands.

BACKGROUND OF THE INVENTION

Benzodiazepine receptor (BzR) ligands are structurally different compounds, which bind to the γ-aminobutyric acid$_A$ ($GABA_A$)/BzR complex. They display a broad pharmacological effect stretching from the full agonistic agents exhibiting anxiolytic, anticonvulsant, sedative-hypnotic and myorelaxant activities to the inverse agonistic agents, which displays anxiogenic, somnolytic and convulsant activities. In between antagonistic agents that elicit no pharmacological effect are present.

The ($GABA_A$)/BzR complex is a membrane-bound pentameric ligand gated chloride ion channel assembled of at least 21 subunits from eight different classes ($\alpha_{1-6}$, $\beta_{1-4}$, $\gamma_{1-4}$, δ, ε, π, θ, and $\rho_{1-3}$).[i,ii] The large number of possible assemblies is somewhat reduced as a completely operational ($GABA_A$)/BzR consist of at least one α, one β and one γ subunit, and the most abundant receptors in vivo contain two α, two β and one γ subunits. Moreover the $\alpha_1\beta_x\gamma_2$, $\alpha_2\beta_x\gamma_2$, $\alpha_3\beta_x\gamma_2$ and $\alpha_5\beta_x\gamma_2$ subtype assemblies are regard as the major benzodiazepine binding receptors, the benzodiazepine binding-site being located at the interface between the α and the γ subunit. Recent studies with transgenic mice and subtype selective compounds clearly suggest that receptors with different subtype composition are associated with different physiological effect e.g. $\alpha_1$-containing receptors mediate sedation and anterograde amnesia, $\alpha_2$-, and/or $\alpha_3$-containing receptors are involved in anxiolytic activity, and $\alpha_5$-containing receptors might be associated with cognition and memory.[iii,iv]

A broad spectrum of BzR binding non-benzodiazepines has been presented and among the most potent are compounds belonging to the following classes cyclopyrrolones, 2-arylpyrazoloquinolines, β-carbolines, pyridodiindoles, triazoloqunioxalines, pyrimidin-5(6H)-ones, and quinolines. Structure-activity relationship of 136 different ligands from ten structurally different classes of compounds was applied in the creation of a comprehensive pharmacophore model for the BZ receptor. The model was developed under the hypothesis that BZ receptor agonists, inverse agonists, and antagonists all share the same binding pocket.

SUMMARY OF THE PRESENT INVENTION

The present invention relates to novel $GABA_A$/BzR ligands, in particular different isozoloquinolinyl derivatives.

Recently, a series of synthetic flavones derivatives were used for the further development of the pharmacophore model.[v,vi] In the present application a series of novel ligands developed through the pharmacophore model i.e. isothiazoloquinolinones (I), isoxazoloquinolinones (II), and isothiazoloquinolinyl amides (III) is presented. (The Roman numbers relates to the formulas of FIG. 1). The ligands are somewhat structurally different, but developed through essentially the same diversified synthetic routes. The proposed binding mode of the novel ligands are showed in FIG. 1. FIG. 1 shows three novel BzR ligands in the pharmacophore model representation.

In FIG. 1 $H_1$ and $H_2$ represent hydrogen bond donor and hydrogen bond acceptor sites, respectively. $H_2/A_3$ is a bifunctional site with ability to both accept and donate a hydrogen bond. $L_1$, $L_2$ and $L_3$ are lipophilic pockets and $S_1$-$S_5$ denotes regions of steric repulsive ligand-receptor interactions (receptor essential volume). The three classes of compounds I, II and III all seams to fulfill the requirements necessary for a strong binding to the BzR. Compounds belonging to class I and II have the ability to donate a hydrogen bond to $A_2$ through NH(6) and accept hydrogen bonds from $H_1$ through N(2) and $H_2$ through the O=C(4) oxygen. Moreover the fused benzene ring and the phenyl group occupy the lipophilic pockets $L_1$ and $L_2$, respectively. The compounds belonging to class III binds similar to a class I or II compound, but with the ability to form possibly two additional hydrogen bonds. The oxygen of the amide moiety might function as an additional hydrogen bond acceptor to the $H_1$, and the NH moiety might be involved as a hydrogen bond donor to the $A_3$ site. The fused benzene ring and the carbamoyl chain occupy the lipophilic pockets $L_1$ and $L_2$, respectively. The $L_1$/$L_2$ lipophilic pocket was probed by introducing a small number of substituents, especially for the class I compounds, in the position corresponding to this region.

DESCRIPTION OF THE PRESENT INVENTION

The present invention relates to novel $GABA_A$/BzR ligands of isothiazoloquinolinone derivatives of the formulas I and III, as well as), isoxazoloquinolinone derivatives of formula II

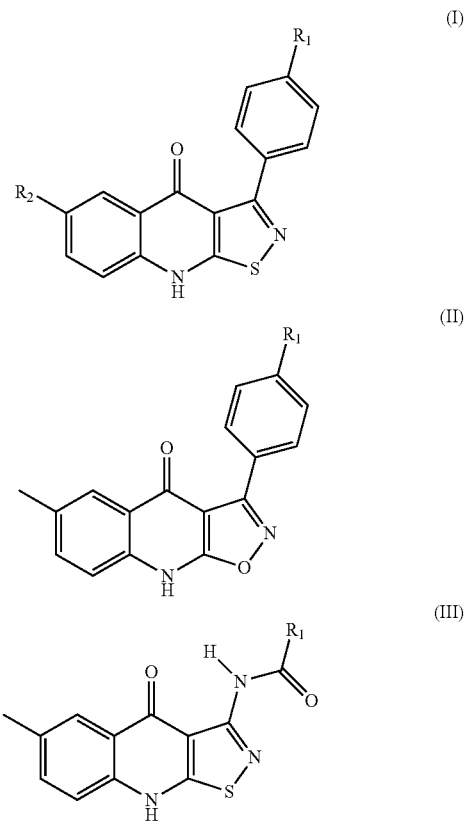

wherein
$R_1$ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and $R_2$ is selected from the group consisting of hydrogen, halogen and alkyl having 1 to 2 carbon atoms, or a pharmaceutically acceptable salt thereof.

In a preferred embodiment $R_1$ being halogen is selected from the group consisting of bromo and fluoro.

In a preferred embodiment $R_2$ being halogen is selected from the group consisting of bromo and fluoro.

In a preferred embodiment $R_1$ being alkoxy is selected from the group consisting of methoxy and ethoxy.

In a preferred embodiment $R_1$ being alkyl is methyl, ethyl or propyl.

In a preferred embodiment $R_1$ being haloalkyl is trifluoromethyl.

In a preferred embodiment the active compound is selected from the group of

6-Methyl-3-(4-methylphenyl)isothiazolo[5,4-b]quinolin-4(9H)-one (19)

6-Methyl-3-phenylisothiazolo[5,4-b]quinolin-4(9H)-one (20)

3-(4-Bromophenyl)-6-methylisothiazolo[5,4-b]quinolin-4(9H)-one (21)

3-(4-Methoxyphenyl)-6-methylisothiazolo[5,4-b]quinolin-4(9H)-one (22)

6-Methyl-3-(4-nitrophenyl)-isothiazolo[5,4-b]quinolin-4(9H)-one (23)

6-Bromo-3-(4-methylphenyl)isothiazolo[5,4-b]quinolin-4(9H)-one (24)

6-Methyl-3-(4-methylphenyl)isoxazolo[5,4-b]quinolin-4(9H)-one (25)

6-Methyl-3-phenyl-isoxazolo[5,4-b]quinolin-4(9H)-one (26)

6-Methyl-3-(4-nitrophenyl)isoxazolo[5,4-b]quinolin-4(9H)-one (27)

N-(6-methyl-4-oxo-4,9-dihydroisothiazolo[5,4-b]quinolin-3-yl)butanamide

N-(6-methyl-4-oxo-4,9-dihydroisothiazolo[5,4-b]quinolin-3-yl) propanamide

A second aspect of the invention relates to compounds of the general formulas (I), (II) and (III)

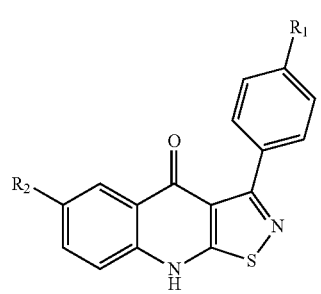
(I)

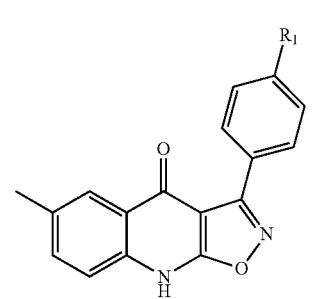
(II)

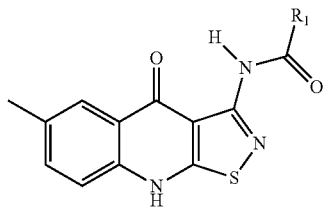
(III)

wherein $R_1$ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and $R_2$ is selected from the group consisting of hydrogen, halogen and alkyl having 1 to 2 carbon atoms, or a pharmaceutically acceptable salt thereof for use in treating anxiolytic, anticonvulsant, sedative-hypnotic and myorelaxant conditions as well as anxiogenic, somnolytic and convulsant conditions.

In a preferred embodiment $R_1$ being halogen is selected from the group consisting of bromo and fluoro.

In a preferred embodiment $R_2$ being halogen is selected from the group consisting of bromo and fluoro.

In a preferred embodiment $R_1$ being alkoxy is selected from the group consisting of methoxy and ethoxy.

In a preferred embodiment $R_1$ being alkyl is methyl, ethyl or propyl.

In a preferred embodiment $R_1$ being haloalkyl is trifluoromethyl.

In a preferred embodiment the active compound is selected from the group of

6-Methyl-3-(4-methylphenyl)isothiazolo[5,4-b]quinolin-4(9H)-one (19)

6-Methyl-3-phenylisothiazolo[5,4-b]quinolin-4(9H)-one (20)

3-(4-Bromophenyl)-6-methylisothiazolo[5,4-b]quinolin-4(9H)-one (21)

3-(4-Methoxyphenyl)-6-methylisothiazolo[5,4-b]quinolin-4(9H)-one (22)

6-Methyl-3-(4-nitrophenyl)-isothiazolo[5,4-b]quinolin-4(9H)-one (23)

6-Bromo 3-(4-methylphenyl)isothiazolo[5,4-b]quinolin-4(9H)-one (24)

6-Methyl-3-(4-methylphenyl)isoxazolo[5,4-b]quinolin-4(9H)-one (25)

6-Methyl-3-phenyl-isoxazolo[5,4-b]quinolin-4(9H)-one (26)

6-Methyl-3-(4-nitrophenyl)isoxazolo[5,4-b]quinolin-4(9H)-one (27)

N-(6-methyl-4-oxo-4,9-dihydroisothiazolo[5,4-b]quinolin-3-yl)butanamide

N-(6-methyl-4-oxo-4,9-dihydroisothiazolo[5,4-b]quinolin-3-yl)propanamide

A third aspect of the invention relates to a pharmaceutical composition comprising as an active ingredient one or more of the compounds of the general formulas (I), (II) and (III)

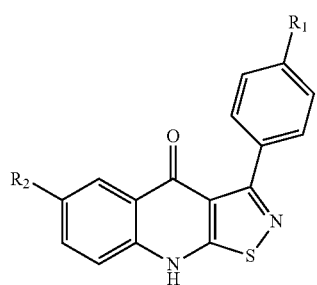

(II)

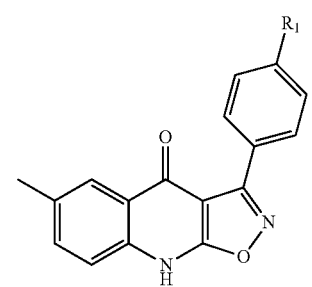

(III)

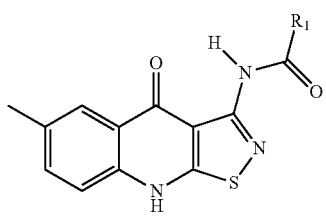

wherein
R₁ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and
R₂ is selected from the group consisting of hydrogen, halogen and alkyl having 1 to 2 carbon atoms, or a pharmaceutically acceptable salt thereof in combination with one or more excipients.

In a preferred embodiment R₁ being halogen is selected from the group consisting of bromo and fluoro.

In a preferred embodiment R₂ being halogen is selected from the group consisting of bromo and fluoro.

In a preferred embodiment R₁ being alkoxy is selected from the group consisting of methoxy and ethoxy.

In a preferred embodiment R₁ being alkyl is methyl, ethyl or propyl.

In a preferred embodiment R₁ being haloalkyl is trifluoromethyl.

In a preferred embodiment the active compound is selected from the group of
 6-Methyl-3-(4-methylphenyl)isothiazolo[5,4-b]quinolin-4(9H)-one (19)
 6-Methyl-3-phenylisothiazolo[5,4-b]quinolin-4(9H)-one (20)
 3-(4-Bromophenyl)-6-methylisothiazolo[5,4-b]quinolin-4(9H)-one (21)
 3-(4-Methoxyphenyl)-6-methylisothiazolo[5,4-b]quinolin-4(9H)-one (22)
 6-Methyl-3-(4-nitrophenyl)-isothiazolo[5,4-b]quinolin-4(9H)-one (23)
 6-Bromo-3-(4-methylphenyl)isothiazolo[5,4-b]quinolin-4(9H)-one (24)
 6-Methyl-3-(4-methylphenyl)isoxazolo[5,4-b]quinolin-4(9H)-one (25)
 6-Methyl-3-phenyl-isoxazolo[5,4-b]quinolin-4(9H)-one (26)
 6-Methyl-3-(4-nitrophenyl)isoxazolo[5,4-b]quinolin-4(9H)-one (27)
 N-(6-methyl-4-oxo-4,9-dihydroisothiazolo[5,4-b]quinolin-3-yl)butanamide
 N-(6-methyl-4-oxo-4,9-dihydroisothiazolo[5,4-b]quinolin-3-yl)propanamide A fourth aspect of the invention relates to a method for treating anxiolytic, anticonvulsant, sedative-hypnotic and myorelaxant conditions as well as anxiogenic, somnolytic and convulsant conditions in mammals, including humans, by administering a therapeutic amount of one or more of the compounds of the general formulas (I), (II) and (III)

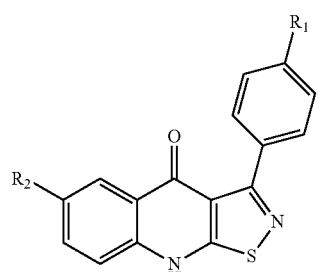

(III)

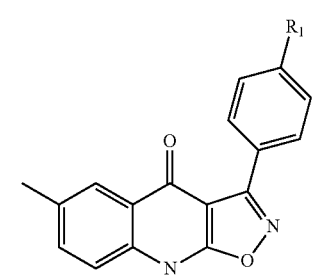

(II)

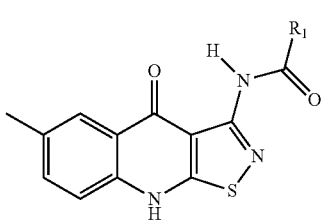

(III)

wherein
R₁ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and
R₂ is selected from the group consisting of hydrogen, halogen and alkyl having 1 to 2 carbon atoms, or a pharmaceutically acceptable salt thereof in combination with one or more excipients.

In a preferred embodiment R₁ being halogen is selected from the group consisting of bromo and fluoro.

In a preferred embodiment R₂ being halogen is selected from the group consisting of bromo and fluoro.

In a preferred embodiment R₁ being alkoxy is selected from the group consisting of methoxy and ethoxy.

In a preferred embodiment R₁ being alkyl is methyl, ethyl or propyl.

In a preferred embodiment $R_1$ being haloalkyl is trifluoromethyl.

In a preferred embodiment the active compound is selected from the group of

6-Methyl-3-(4-methylphenyl)isothiazolo[5,4-b]quinolin-4(9H)-one (19)

6-Methyl-3-phenylisothiazolo[5,4-b]quinolin-4(9H)-one (20)

3-(4-Bromophenyl)-6-methylisothiazolo[5,4-b]quinolin-4(9H)-one (21)

3-(4-Methoxyphenyl)-6-methylisothiazolo[5,4-b]quinolin-4(9H)-one (22)

6-Methyl-3-(4-nitrophenyl)-isothiazolo[5,4-b]quinolin-4(9H)-one (23)

6-Bromo-3-(4-methylphenyl)isothiazolo[5,4-b]quinolin-4(9H)-one (24)

6-Methyl-3-(4-methylphenyl)isoxazolo[5,4-b]quinolin-4(9H)-one (25)

6-Methyl-3-phenyl-isoxazolo[5,4-b]quinolin-4(9H)-one (26)

6-Methyl-3-(4-nitrophenyl)isoxazolo[5,4-b]quinolin-4(9H)-one (27)

N-(6-methyl-4-oxo-4,9-dihydroisothiazolo[5,4-b]quinolin-3-yl)butanamide

N-(6-methyl-4-oxo-4,9-dihydroisothiazolo[5,4-b]quinolin-3-yl)propanamide

The term "pharmaceutically acceptable salt" means either an acid addition salt or a basic addition salt which is compatible with the treatment of patients. A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium, monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate. The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The present invention will be described more in detail in the following with reference to examples for producing the active compounds of the invention, as well as test results showing the activity of the compounds.

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of formula I. The optically active forms of the compound of the invention may be prepared, for example, by chiral chromatographic separation of a racemate or chemical or enzymatic resolution methodology, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes. The present invention includes any geometrical isomer of a compound of formula I. It will further be understood that the present invention encompasses tautomers of the compounds of formula I.

It will also be understood by those of skill in the art that certain compounds of the present invention may exist in solvated, for example hydrated, as well as unsolvated forms. It will further be understood that the present invention encompasses all such solvated forms of the compounds of formula I.

Chemistry

All compounds belonging to classes I, II and III are as far as presently known all novel compounds. The synthesis of the compounds is shown in schemes 1 and 2 below.

In the reaction schemes shown the key intermediate 5 and 6 were obtained by treatment of anthranilic acids with carbon disulfide and iodomethane followed by cyclization in refluxing acetic anhydride. Nucleophilic addition of lithium enolates of various acetophenones yielded the keto-enols 7 to 12. Cyclization in sodium methoxide gave the corresponding quinolone derivative 13 to 18. The isothiazoloquinolinones 19-24 were obtained by treatment of the quinolone derivative 13-18 with hydroxylamine-O-sulfonic acid. The isoxazoloquinoazolones 25-27 could be obtained by treatment with hydroxylamine and cyclization with Amberlyst 15, subsequently. Following essentially the same route utilizing a nuclophilic addition of a lithium salt of acetonitrile to 5 as the key step led to the synthesis of cyano derivative 29. Treatment with hydroxylamine-O-sulfonic acid gave aminothioisoxazole 30, which due to limited stability in solution was used as a crude. Treatment with acid chlorides yielded isothiazoloquinolinyl amides 31 and 32. It was believed that strong binders to the BzR could be obtained by exchanging the alkyl chain to various aromatics. Unfortunately, the solubility of a few other isothiazoloquinolinyl amides synthesized was too poor to enable easy purification and further biological evaluation of the compounds.

Scheme 1[a]

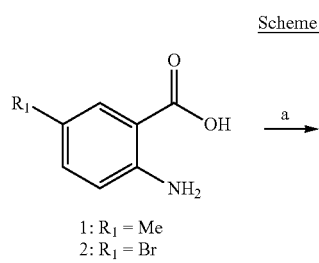

1: $R_1$ = Me
2: $R_1$ = Br

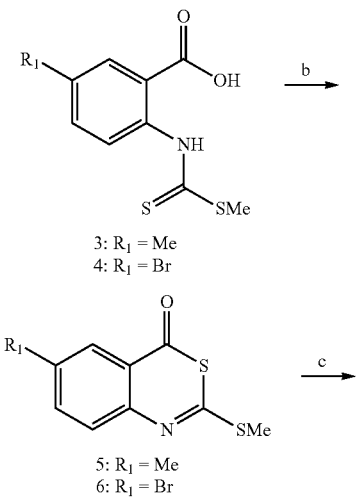

3: $R_1$ = Me
4: $R_1$ = Br

5: $R_1$ = Me
6: $R_1$ = Br

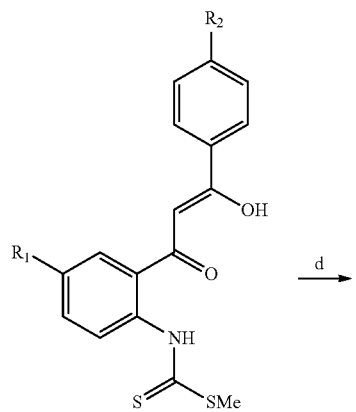

7: $R_1$ = Me, $R_2$ = Me
8: $R_1$ = Me, $R_2$ = H
9: $R_1$ = Me, $R_2$ = Br
10: $R_1$ = Me, $R_2$ = OMe
11: $R_1$ = Me, $R_2$ = NO$_2$
12: $R_1$ = Br, $R_2$ = Me

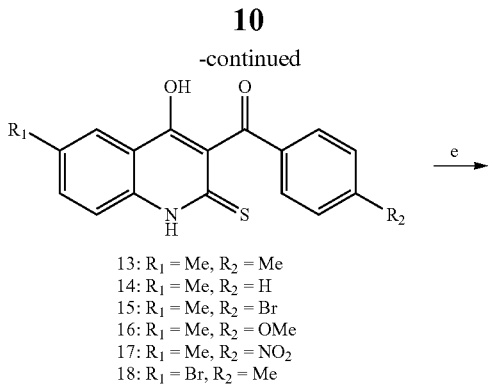

13: $R_1$ = Me, $R_2$ = Me
14: $R_1$ = Me, $R_2$ = H
15: $R_1$ = Me, $R_2$ = Br
16: $R_1$ = Me, $R_2$ = OMe
17: $R_1$ = Me, $R_2$ = NO$_2$
18: $R_1$ = Br, $R_2$ = Me

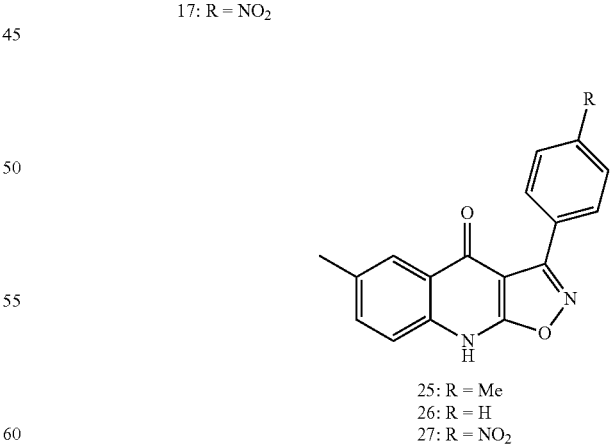

19: $R_1$ = Me, $R_2$ = Me
20: $R_1$ = Me, $R_2$ = H
21: $R_1$ = Me, $R_2$ = Br
22: $R_1$ = Me, $R_2$ = OMe
23: $R_1$ = Me, $R_2$ = NO$_2$
24: $R_1$ = Br, $R_2$ = Me

13: R = Me
14: R = H
17: R = NO$_2$

25: R = Me
26: R = H
27: R = NO$_2$

[a]Conditions: (a) CS$_2$, NEt$_3$, dioxane, 5° C., 18 h, then MeI, 5° C., 1 h. (b) Ac$_2$O, reflux, 1 h. (c) LDA, 4′-acetophenones, THF, -78° C., 1 h, then 5 or 6, -78° C. to -30° C., 3 h. (d) NaOMe, MeOH, 0° C., 3 h. (e)H$_2$NOSO$_3$H, LiOH, MeOH, rt, 24 h. (f) NaOAc, H$_2$NOH•HCl, EtOH, reflux, 5 h, then Amberlyst 15, MeCN, reflux, 2 h.

Scheme 2[a]

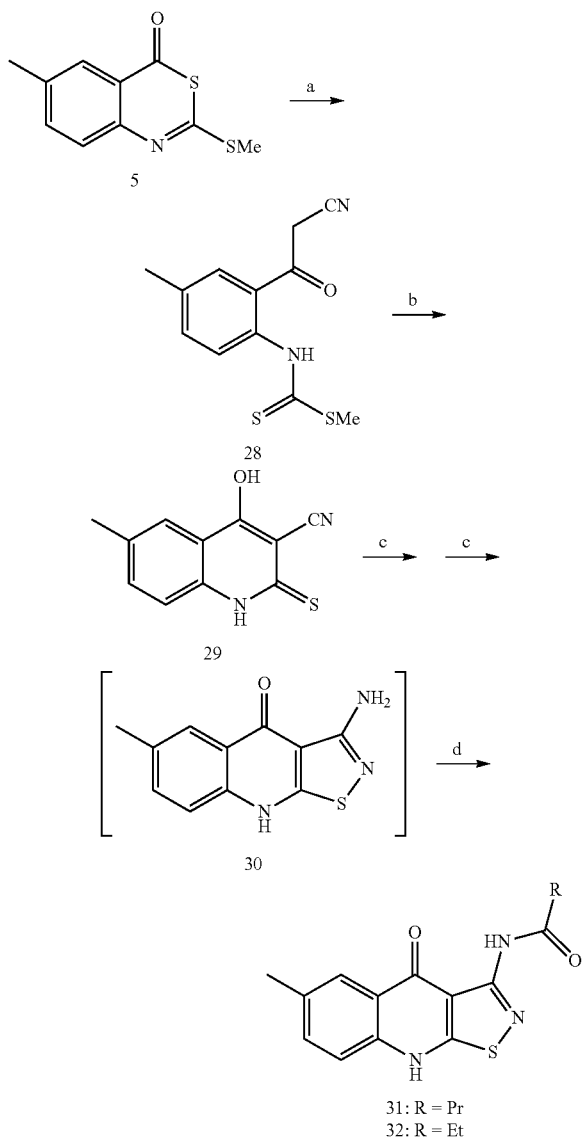

31: R = Pr
32: R = Et

[a]Conditions: (a) LDA, MeCN, THF, -78° C. to -20° OC., 1 h, then 5, -20° C., 1.5 h. (b) NaOMe, MeOH, 0° C., 1 h. (c) H$_2$NOSO$_3$H, NaHCO$_3$, MeOH, DMF, rt, 2 h, then RCOCl, pyridine, DMF, 5 h.

EXPERIMENTAL SECTION

Reagents and solvents were used from commercial sources without purification. $^1$H and $^{13}$C NMR were recorded at room temperature with a Bruker ARX300 or a Bruker DRX400 spectrometer. The spectra were recorded in CDCl$_3$, DMSO-d$_6$, and CD$_3$OD, and the solvent signals (7.27 and 77.0, 2.50 and 39.5 or 3.31 and 49.0 ppm, respectively) were used as reference. The raw data were transformed and the spectra were evaluated with the standard Bruker UXNMR software (rev. 941001). Analytical thin layer chromatography (TLC) was performed on Kiselgel 60 F$_{254}$ plates (Merck). Column chromatography was performed on SiO$_2$ (Matrex LC-gel: 60A, 35-70 MY, Grace). Melting points (uncorrected) were determined with a Reichert microscope. EI mass spectra were recorded at 70 eV with a Jeol SX102 spectrometer and ESI spectra were recorded with Micromass Q-TOF Micro. The purity of the assayed compounds was verified with $^1$H NMR and HPLC, and only used if more than 98% pure.

5-Methyl-2-{[(methylsulfanyl)carbonothioyl]amino}benzoic acid (3)

To a solution of 2-amino-5-methylbenzoic acid (2.52 g, 16.7 mmol) and carbon disulfide (2.01 mL, 33.9 mmol) in 45 mL of dry 1,4-dioxane was added NEt$_3$ (5.58 mL, 40.0 mmol) and the mixture were stirred under N$_2$ atmosphere at 5° C. for 18 hours. Iodomethane (1.14 mL, 18.4 mmol) was added dropwise and the mixture was stirred as 5° C. for 1 hour. The reaction was poured into 25 mL of an aqueous solution of HCl (1M) and the mixture was concentrated to half its volume under reduced pressure and extracted three times with 75 mL of EtOAc. The combined organic layers were dried over MgSO$_4$ and concentrated under reduced pressure. The residue was recrystallized from chloroform to give 3 as a yellow solid (3.25 g, 81%). mp: 199° C.
$^1$H NMR (400 MHz, MeOD-d$_4$) δ 8.82 (1H, d, J=8.2 Hz), 7.90 (1H, s), 7.38 (1H, d, J=8.2 Hz), 2.63 (3H, s), 2.35 (3H, s); $^{13}$H NMR (100 MHz, MeOD-d$_4$) δ 189.2, 161.4, 130.9, 126.5, 125.4, 123.2, 114.2, 110.7, 11.3, 8.9; HRMS (ESI): for C$_{10}$H$_{12}$NO$_2$S$_2$ calcd: 242.0309; [M+H]. Found: 242.0316.

5-Bromo-2-{[(methylsulfanyl)carbonothioyl]amino}benzoic acid (4) was prepared and purified according to the procedure described for 3, starting from 2-amino-5-bromobenzoic acid. The reaction yielded 4 (80%) as pale crystals (mp: 185° C.).
$^1$H NMR (300 MHz, CDCl$_3$) δ 11.81 (1H, s), 9.15 (1H, d, J=9.1 Hz), 8.28 (1H, d, J=2.4 Hz), 7.72 (1H, dd, J=9.1 and 2.4 Hz), 2.69 (3H, s); $^{13}$C NMR (100 MHz, CDCl$_3$) δ 199.6, 169.8, 142.1, 137.2, 135.1, 125.1 121.7, 117.9, 18.7; HRMS (ESI): for C$_9$H$_9$BrNO$_2$S$_2$ calcd: 305.9258; [M+H]. Found: 305.9261.

6-Methyl-2-(methylsulfanyl)-4H-3,1-benzothiazin-4-one (5)

Compound 3 (2.85 g, 11.8 mmol) was dissolved in 50 mL of acetic anhydride and heated at reflux for 1 hour. The mixture was cooled to room temperature and the precipitate was filtered off. The crude product was recrystallized from ethyl alcohol to give 5 as white needle-shaped crystals (2.17 g, 83%). mp: 113.6° C.
$^1$H NMR (400 MHz, CDCl$_3$+5% MeOD-d4) δ 7.95 (1H, s), 7.57 (2H, bs), 2.70 (3H, s), 2.45 (3H, s); $^{13}$C NMR (100 MHz, CDCl3+5% MeOD-d4) δ 183.5, 162.3, 146.3, 138.0, 137.1, 129.8, 124.7, 119.1, 21.3, 14.2; HRMS (ESI): for C$_{10}$H$_{10}$NOS$_2$ calcd: 224.0204; [M+H]. Found: 224.0201.

6-Bromo-2-(methylsulfanyl)-4H-3,1-benzothiazin-4-one (6) was prepared and purified according to the procedure described for 5, starting from 4. The reaction yielded 6 (89%) as pale crystals (mp: 118.9° C.).
$^1$H NMR (400 MHz, CDCl$_3$) δ 8.01 (1H, d, J=2.4 Hz), 7.60 (1H, dd, J=8.6 and 2.4 Hz), 7.31 (1H, d, J=8.6 Hz), 2.50 (3H, s); $^{13}$C NMR (100 MHz, CDCl$_3$) δ 182.0, 164.9, 146.8, 138.6, 131.5, 127.6, 121.0, 120.1, 14.4; HRMS (ESI): for C$_9$H$_7$BrNOS$_2$ calcd: 287.9152; [M+H]. Found: 287.9141.

Methyl {2-[(2Z)-3-hydroxy-3-(4-methylphenyl)prop-2-enoyl]-4-methylphenyl}-dithiocarbamate (7)

A solution of 1.6 M n-BuLi (10.4 mL, 16.7 mmol) in hexanes was added to a solution of diisopropylamine (2.42 mL, 17.4 mmol) in 20 mL of THF under N$_2$ atmosphere at −78° C. The solution was heated to 0° C. and stirred for 5 min and then once again cooled to −78° C. To the resultant LDA solution was added a solution of 4'-methylacetophenone (2.28 mL, 16.7 mmol) in 5 mL of THF and the mixture was stirred for one hour. A solution of 5 in 20 mL of THF was slowly added and the mixture was slowly heated to −30° C. over a period of 3 hours, while monitored on TLC. The reaction was poured onto 35 mL of an aqueous solution of HCl (1M) and the mixture was concentrated to half its volume. The residue was extracted with 100 mL of EtOAc and the organic layer was washed with Brine, dried over $MgSO_4$ and concentrated under reduced pressure. The residue was dried under vacuum in order to remove a substantial fraction of unreacted acetophenone and the crude product was triturated from methanol to give 7 as a yellow solid (2.18 g, 91%). Purification of the remaining solution through chromatography generally gave an increased yield, especially if the remaining amount of acetophenone is significant. Elution was done with a mixture of n-heptane/toluene/acetone (75:75:1). mp: 144° C.

$^1$H NMR (400 MHz, DMSO-d6) δ 16.64 (1H, s), 11.69 (1H, s), 7.90 (2H, d, J=8.2 Hz), 7.68 (1H, d, J=1.4 Hz), 7.44 (1H, dd, J=8.1 and 1.4 Hz), 7.37 (2H, d, J=8.2 Hz), 7.37 (1H, d, J=8.1 Hz), 6.83 (1H, s), 2.57 (3H, s), 2.40 (3H, s), 2.39 (3H, s); $^{13}$C NMR (100 MHz, DMSO-d6) δ 199.9, 186.1, 183.9, 143.6, 137.7, 135.1, 132.8, 132.7, 131.6, 129.6, 129.5, 129.0, 127.2, 96.4, 21.2, 20.5, 18.1; HRMS (ESI): for $C_{19}H_{20}NO_2S_2$ calcd: 358.0935; [M+H]. Found: 358.0941.

Methyl [2-((2Z)-3-hydroxy-3-phenyl-prop-2-enoyl]-4-methylphenyl]dithiocarbamate (8) was prepared and purified according to the procedure described for 7, starting from acetophenone. The reaction yielded 8 (88%) as a yellow solid (mp: 129° C.).

$^1$H NMR (400 MHz, CDCl$_3$) δ 16.20 (1H, s), 11.54 (1H, s), 8.44 (1H, d, J=8.4 Hz), 7.75 (2H, d, J=7.2 Hz), 7.39 (1H, d, J=1.4 Hz), 7.35 (1H, d, J=7.3 Hz), 7.28 (2H, t, J=7.8 Hz), 7.13 (1H, dd, J=8.4 and 1.4 Hz), 6.54 (1H, s), 2.20 (3H, s), 2.16 (3H, s); $^{13}$C NMR (100 MHz, CDCl$_3$) δ 198.4, 193.2, 180.8, 137.1, 135.3, 133.9, 133.6, 132.9, 129.6, 129.0, 129.0, 127.2, 127.2, 126.7, 124.4, 95.5, 21.2, 18.7; HRMS (ESI): for $C_{18}H_{18}NO_2S_2$ calcd: 344.0779; [M+H]. Found: 344.0778.

Methyl {2-[(2Z)-3-(4-bromophenyl)-3-hydroxy-prop-2-enoyl]-4-methylphenyl}-dithiocarbamate (9) was prepared and purified according to the procedure described for 7, starting from 4'-bromoacetophenone. The reaction yielded 9 (83%) as a yellow solid (mp: 172° C.).

$^1$H NMR (300 MHz, CDCl$_3$) δ 16.18 (1H, s), 11.60 (1H, s), 8.61 (1H, d, J=8.5 Hz), 7.82 (2H, d, J=8.5 Hz), 7.63 (2H, d, J=8.5 Hz), 7.59 (1H, d, J=1.5 Hz), 7.37 (1H, d, J=8.5 Hz), 6.72 (1H, s), 2.69 (3H, s), 2.42 (3H, s); $^{13}$C NMR (100 MHz, CDCl$_3$) δ 198.7, 193.2, 179.6, 137.0, 135.4, 133.7, 132.9, 132.3, 132.3, 129.6, 128.6, 128.6, 127.7, 126.8, 124.7, 95.6, 21.2, 18.7; HRMS (ESI): for $C_{18}H_{17}BrNO_2S_2$ calcd: 421.9884; [M+H]. Found: 421.9889.

Methyl {2-[(2Z)-3-hydroxy-3-(4-methoxyphenyl)prop-2-enoyl]-4-methylphenyl}-dithiocarbamate (10) was prepared and purified according to the procedure described for 7, starting from 4'-methoxyacetophenone. The reaction yielded 10 (85%) as a yellow solid (mp: 138° C.).

$^1$H NMR (400 MHz, DMSO-d6) δ 16.80 (1H, bs), 11.69 (1H, s), 7.99 (2H, d, J=9.0 Hz), 7.68 (1H, d, J=1.5 Hz), 7.43 (1H, dd, J=8.1 and 1.5 Hz), 7.37 (1H, d, J=8.1 Hz), 7.09 (2H, d, J=9.0 Hz), 6.80 (1H, s), 3.86 (3H, s), 2.57 (3H, s), 2.40 (3H, s); $^{13}$C NMR (100 MHz, DMSO-d6) δ 199.9, 184.6, 184.3, 163.3, 137.7, 135.0, 132.6, 132.6, 129.5, 129.4, 129.0, 126.7, 114.3, 114.3, 95.9, 55.6, 20.6, 18.2; HRMS (ESI): for $C_{19}H_{20}NO_3S_2$ calcd: 374.0885; [M+H]. Found: 374.0885.

Bromo {2-[(2Z)-3-hydroxy-3-(4-methylphenyl)prop-2-enoyl]-4-methylphenyl}-dithiocarbamate (12) was prepared and purified according to the procedure described for 7, starting from 6. The reaction yielded 12 (89%) as a yellow solid (mp: 148° C.).

$^1$H NMR (400 MHz, CDCl$_3$) δ 11.94 (1H, s), 8.85 (1H, d, J=8.9 Hz), 7.90 (1H, d, J=2.3 Hz), 7.87 (2H, d, J=8.2 Hz), 7.62 (1H, dd, J=8.9 and 2.3 Hz), 7.31 (2H, d, J=8.2 Hz), 6.68 (1H, s), 2.69 (3H, s), 2.45 (3H, s); $^{13}$C NMR (100 MHz, CDCl$_3$) δ 198.7, 191.8, 181.7, 144.4, 138.8, 135.4, 131.8, 130.8, 129.9, 129.9, 128.1, 127.4, 127.4, 125.6, 117.7, 95.0, 22.0, 18.8; HRMS (ESI): for $C_{18}H_{17}BrNO_2S_2$ calcd: 421.9884; [M+H]. Found: 421.9874.

(4-Hydroxy-6-methyl-2-thioxo-1,2-dihydroquinolin-3-yl)(4-methylphenyl)methanone (13)

Keto-enol 7 (2.12 g, 5.93 mmol) was added to 100 mL of a 0.5 M solution of sodium methoxide in methanol and the mixture was stirred at 0° C. for 3 hours. A 1.0 M solution of hydrochloric acid (53 mL) was poured onto the reaction and the mixture was concentrated to less than half its volume under reduced pressure. The obtained slurry was stirred for 30 min at room temperature and then filtrated. The precipitate was washed with 20 mL of water and 20 mL of methanol, subsequently. The crude product was precipitated from acetone to give 13 as a yellow solid (1.70 g, 93%). mp: 280° C.;

$^1$H NMR (400 MHz, DMSO-d6) δ 13.17 (1H, s), 11.57 (1H, bs), 7.90 (1H, bs), 7.70 (2H, d, J=8.2 Hz), 7.58 (1H, d, J=8.5 Hz), 7.53 (1H, dd, J=8.5 and 1.5 Hz); 7.28 (2H, d, J=8.2 Hz), 2.40 (3H, s), 2.36 (3H, s); $^{13}$C NMR (100 MHz, DMSO-d6) δ 192.2, 177.4, 155.9, 143.4, 138.4, 134.7, 133.5, 133.0, 129.2, 129.2, 129.1, 129.1, 122.4, 122.4, 117.1, 116.4, 21.2, 20.8; HRMS (ESI): for $C_{18}H_{16}NO_2S$ calcd: 310.0902; [M+H]. Found: 310.0902.

(4-Hydroxy-6-methyl-2-thioxo-1,2-dihydroquinolin-3-yl)-4-phenyl-methanone (14) was prepared and purified according to procedure described for 13, starting from 8. The reaction yielded 14 (94%) as a yellow solid (mp: 259° C.).

$^1$H NMR (400 MHz, DMSO-d6) δ 7.88 (1H, s), 7.80 (2H, d, J=7.4 Hz), 7.58 (3H, m), 7.47 (2H, t, J=7.4 Hz), 2.41 (3H, s); $^{13}$C NMR (100 MHz, DMSO-d6) δ 192.7, 177.3, 156.1, 138.5, 137.0, 134.0, 133.6, 133.0, 133.0, 128.9, 128.9, 128.6, 128.6, 122.4, 122.2, 117.1, 116.4, 20.8; HRMS (ESI): for $C_{17}H_{14}NO_2S$ calcd: 296.0745; [M+H]. Found: 296.0758.

(4-Bromophenyl)(4-hydroxy-6-methyl-2-thioxo-1,2-dihydroquinolin-3-yl)methanone (15) was prepared and purified according to the procedure described for 13, starting from 9. The reaction yielded 15 (98%) as a yellow solid (mp: 275° C.).

$^1$H NMR (400 MHz, DMSO-d6) δ 7.92 (1H, s), 7.73 (2H, d, J=8.5 Hz), 7.68 (2H, d, J=8.5 Hz), 7.58 (1H, d, J=8.5 Hz), 7.56 (1H, d, J=8.5 Hz), 2.41 (3H, s); $^{13}$C NMR (100 MHz, DMSO-d6) δ 191.8, 177.0, 156.5, 138.5, 136.2, 133.7, 133.7, 133.0, 133.0, 131.8, 130.9, 127.0, 122.5, 121.5, 117.2, 116.4, 20.8; HRMS (ESI): for $C_{17}H_{13}BrNO_2S$ calcd: 373.9850; [M+H]. Found: 373.9849.

(4-Hydroxy-6-methyl-2-thioxo-1,2-dihydroquinolin-3-yl)(4-methoxyphenyl)methanone (16) was prepared and purified according to procedure described for 13, starting from 10. The reaction yielded 16 (93%) as a yellow solid (mp: 260° C.).

$^1$H NMR (400 MHz, DMSO-d6) δ 12.05 (1H, bs), 7.75 (1H, d, J=1.5 Hz), 7.72 (2H, dt, J=8.9 and 2.8 Hz), 7.44 (1H, d, J=8.4 Hz), 7.37 (1H, dd, J=8.4 and 1.5 Hz), 6.95 (2H, dt, J=8.9 and 2.8 Hz); $^{13}$C NMR (100 MHz, DMSO-d6) δ 193.6, 175.3, 162.7, 161.8, 138.7, 132.6, 131.6, 131.3, 131.3, 123.4, 121.8, 119.9, 116.2, 113.6, 113.6, 55.5, 20.8; HRMS (ESI): for $C_{18}H_{16}NO_3S$ calcd: 326.0851; [M+H]. Found: 326.0849.

(4-Hydroxy-6-methyl-2-thioxo-1,2-dihydroquinolin-3-yl)(4-nitrophenyl)methanone (17) was prepared and purified according to the procedure described for 7, starting from 4'-nitroacetophenone. The reaction yielded a mixture of the keto-enol compound 11 and 17, which was applied to the condition described for the synthesis of 13. The two-step reaction yielded 17 (37%) as a yellow solid (mp: 247° C.).

$^1$H NMR (400 MHz, DMSO-d6,) δ 13.42 (1H, bs), 11.57 (1H, s), 8.29 (2H, d, J=8.7 Hz), 7.92 (2H, d, J=8.7 Hz), 7.80 (1H, s), 7.50 (1H, dd, J=8.4 and 1.6 Hz), 7.24 (1H, d, J=8.4 Hz), 2.37 (3H, s); $^{13}$C NMR (100 MHz, DMSO-d6) δ 191.4, 176.9, 157.0, 149.7, 142.0, 138.7, 133.9, 133.2, 130.0, 130.0, 123.9, 123.9, 122.6, 121.0, 117.3, 116.5, 20.8; HRMS (ESI): for $C_{17}H_{13}N_2O_4S$ calcd: 341.0596; [M+H]. Found: 341.0601.

(6-Bromo-4-hydroxy-2-thioxo-1,2-dihydroquinolin-3-yl)(4-methylphenyl)methanone (18) was prepared and purified according to the procedure described for 13, starting from 12. The reaction yielded 18 (92%) as a yellow solid (mp: 280 (decomp.) ° C.).

$^1$H NMR (400 MHz, DMSO-d6) δ 8.24 (1H, d, J=2.0 Hz), 7.84 (1H, dd, J=8.9 and 2.0 Hz), 7.70 (2H, d, J=8.0 Hz), 7.58 (1H, d, J=8.9 Hz), 7.28 (2H, d, J=8.0 Hz), 2.36 (3H, s); $^{13}$C NMR (100 MHz, DMSO-d6) δ 192.0, 178.5, 155.3, 143.5, 139.1, 134.6, 134.4, 129.2, 129.2, 129.1, 129.1, 125.4, 123.1, 119.1, 118.6, 115.6, 21.2; HRMS (ESI): for $C_{17}H_{13}BrNO_2S$ calcd: 373.9850; [M+H]; found: 373.9841.

6-Methyl-3-(4-methylphenyl)isothiazolo[5,4-b]quinolin-4(9H)-one (19)

To a solution of 13 (80 mg, 0.259 mmol) in 25 mL of methanol was added a solution of hydroxylamine-O-sulfonic acid (102.6 mg, 0.907 mol) and lithium hydroxide (38.1 mg, 0.907 mmol) in 3 mL of methanol and the mixture was stirred at room temperature for 30 hours. The reaction mixture was concentrated under reduced pressure and applied to flash chromatography. Elution with heptane/EtOAc (3:1) gave 19 as a white solid (44 mg, 55%). mp: 330° C.;

$^1$H NMR (400 MHz, DMSO-d6) δ 12.80 (1H, s), 8.02 (1H, bs), 7.73 (2H, d, J=7.9 Hz), 7.61 (1H, dd, J=8.4 and 1.5 Hz), 7.45 (1H, d, J=8.4 Hz), 7.26 (2H, d, J=7.9 Hz), 2.43 (3H, s), 2.39 (3H, s); $^{13}$C NMR (100 MHz, DMSO-d6) δ 172.7, 166.8, 166.0, 138.6, 137.7, 134.5, 132.8, 132.3, 129.4, 129.4, 128.0, 128.0, 125.6, 123.6, 117.3, 117.3, 21.0, 20.7; HRMS (ESI): for $C_{18}H_{15}N_2OS$ calcd: 307.0905; [M+H]. Found: 307.0908.

6-Methyl-3-phenylisothiazolo[5,4-b]quinolin-4(9H)-one (20) was prepared and purified according to the procedure described for 19, starting from 14. The reaction yielded 20 (92%) as a white solid (mp: ?° C.).

$^1$H NMR (400 MHz, DMSO-d6) 12.85 (1H, s), 8.02 (1H, bs), 7.81 (2H, m), 7.61 (1H, dd, J=8.3 and 1.3 Hz), 7.47 (4H, m), 2.43 (3H, s); $^{13}$C NMR (100 MHz, DMSO-d6) δ 172.6, 166.7; 166.0, 137.7, 135.5, 134.5, 132.3, 129.5, 129.0, 127.4, 125.5, 123.6, 117.3, 117.3, 20.6; HRMS (ESI): for $C_{17}H_{13}N_2OS$ calcd: 293.0749 [M+H]. Found: 293.0763.

3-(4-Bromophenyl)-6-methylisothiazolo[5,4-b]quinolin-4(9H)-one (21) was prepared and purified according to the procedure described for 19, starting from 15. The reaction yielded 21 (72%) as a white solid (mp: 357° C.).

$^1$H NMR (400 MHz, DMSO-d6) δ 12.95 (1H, s), 8.02 (1H, d, J=1.9 Hz), 7.79 (2H, dt, J=8.4 and 1.7 Hz), 7.67 (2H, dt, J=8.4 and 1.7 Hz), 7.61 (1H, dd, J=8.4 and 1.9 Hz), 7.47 (1H, d, J=8.4 Hz), 2.43 (3H, s); $^{13}$C NMR (100 MHz, DMSO-d6) δ 172.7, 166.8, 164.7, 137.7, 134.7, 134.6, 132.5, 131.6, 131.6, 130.4, 130.4, 125.5, 123.5, 122.8, 117.4, 117.2, 20.6; HRMS (ESI): for $C_{17}H_{12}BrN_2OS$ calcd: 370.9854; [M+H]. Found: 370.9857.

3-(4-Methoxyphenyl)-6-methylisothiazolo[5,4-b]quinolin-4(9H)-one (22) was prepared and purified according to the procedure described for 19, starting from 16. The reaction yielded 22 (62%) as a white solid (mp: X ° C.).

$^1$H NMR (400 MHz, DMSO-d6) δ 8.03 (1H, s), 7.83 (2H, d, J=8.4 Hz), 7.57 (1H, d, J=8.2 Hz), 7.44 (1H, d, J=8.2 Hz), 7.00 (2H, d, J=8.4 Hz), 3.83 (3H, s), 2.43 (3H, s); $^{13}$C NMR (100 MHz, DMSO-d6) δ 172.7, 167.2, 165.7, 160.0, 138.1, 134.4, 132.1, 131.0, 131.0, 128.2, 125.6, 123.7, 117.6, 117.1, 112.7, 112.7, 55.2, 20.7; HRMS (ESI): for $C_{18}H_{15}N_2OS$ calcd: 323.0854; [M+H]; found: 323.0851.

6-Methyl-3-(4-nitrophenyl)-isothiazolo[5,4-b]quinolin-4(9H)-one (23) was prepared and purified according to the procedure described for 19, starting from 17. The reaction yielded 23 (81%) as a white solid (mp: 343° C.).

$^1$H NMR (400 MHz, DMSO-d6) δ 8.32 (2H, d, J=8.9 Hz), 8.11 (2H, d, J=8.9 Hz), 8.03 (1H, d, J=1.8 Hz), 7.61 (1H, dd, J=8.3 and 1.8 Hz), 7.49 (1H, d, J=8.3 Hz), 2.43 (3H, s); $^{13}$C NMR (100 MHz, DMSO-d6) δ 172.7, 167.2, 163.6, 147.6, 141.5, 138.1, 134.7, 132.4, 130.9, 130.9, 125.4, 123.5, 122.6, 122.6, 117.8, 117.3, 20.7; HRMS (ESI): for $C_{17}H_{12}N_3O_3S$ calcd: 338.0599; [M+H]; found: 338.0599.

6-Bromo-3-(4-methylphenyl)isothiazolo[5,4-b]quinolin-4(9H)-one (24) was prepared and purified according to the procedure described for 19, starting from 18. The reaction yielded 24 (80%) as a white solid (mp: 331° C.).

$^1$H NMR (400 MHz, DMSO-d6) δ 13.01 (1H, s), 8.28 (1H, d, J=2.0 Hz), 7.89 (1H, dd, J=8.6 and 2.0 Hz), 7.71 (2H, d, J=7.7 Hz), 7.51 (1H, d, J=8.6 Hz), 7.26 (2H, d, J=7.7 Hz), $^{13}$C NMR (100 MHz, DMSO-d6) δ 171.5, 167.3, 166.0, 138.7, 138.5, 135.8, 132.5, 129.4, 129.4, 128.4, 128.0, 128.0, 125.3, 120.0, 117.5, 115.3, 21.0; HRMS (ESI): for $C_{17}H_{12}BrN_2OS$ calcd: 370.9854; [M+H]. Found: 370.9852.

6-Methyl-3-(4-methylphenyl)isoxazolo[5,4-b]quinolin-4(9H)-one (25)

A mixture of hydroxylamine hydrochloride (22.6 mg, 0.325 mmol) and sodium acetate (26.6 mg, 0.325 mmol) was stirred in 3 mL of ethyl alcohol for 30 min. The precipitate was filtered off and the clear hydroxylamine solution was added to 13 and the mixture was heated at reflux for 18 hours. The reaction mixture was concentrated under reduced pressure and to the crude oxime was added Amberlyst 15 (20 mg) and 2 mL of acetonitrile and the mixture was heated at reflux under vigorous stirring for 8 hours. The mixture was cooled to room temperature and filtrated through a porous glass filter in order to remove the Amberlyst resin. The residue was purified by chromatography. Elution with n-heptan/EtOAc (3:1) gave 31 as a white solid (5 mg, XX %). mp: X ° C.;

$^1$H NMR (400 MHz, DMSO-d6) δ 13.49 (1H, s), 8.25 (2H, d, J=8.0 Hz), 8.04 (1H, d, J=1.5 Hz), 7.59 (1H, d, J=8.2 Hz and 1.5 Hz), 7.48 (1H, d, J=8.2 Hz), 7.36 (2H, d, J=8.0 Hz), 2.43 (3H, s), 2.40 (3H, s); $^{13}$C NMR (100 MHz, DMSO-d6) δ 172.4, 165.7, 159.8, 140.6, 135.8, 134.4, 132.5, 129.1, 129.1, 129.0, 129.0, 125.6, 124.7, 124.1, 118.0, 98.5, 21.1, 20.6; HRMS (ESI): for $C_{18}H_{15}N_2O_2$ calcd: 291.1134; [M+H]. Found: 291.1139.

6-Methyl-3-phenyl-isoxazolo[5,4-b]quinolin-4(9H)-one (26) was prepared and purified according to the procedure described for 25, starting from 14. The reaction yielded 26 (20%) as a white solid (mp: X ° C.).

$^1$H NMR (400 MHz, DMSO-d6) δ 8.32 (2H, m), 8.03 (1H, s), 7.57 (4H, m), 7.48 (1H, d, J=8.3 Hz), 2.43 (3H, s); $^{13}$C NMR (100 MHz, DMSO-d6) δ 172.4, 165.7, 159.9, 135.8, 134.5, 132.6, 130.8, 129.1, 129.1, 128.5, 128.5, 127.5, 125.6, 124.1, 118.0, 98.5, 20.6; HRMS (ESI): for $C_{17}H_{13}N_2O_2$ calcd: 277.0977; [M+H]. Found: 277.0976.

6-Methyl-3-(4-nitrophenyl)isoxazolo[5,4-b]quinolin-4 (9H)-one (27) was prepared and purified according to the procedure described for 25, starting from 17. The reaction yielded 27 (24%) as a white solid (mp: X ° C.).

$^1$H NMR (400 MHz, DMSO-d6) δ 8.65 (2H, dt, J=9.1 and 2.3 Hz), 8.42 (2H, dt; J=9.1 and 2.3 Hz), 8.06 (1H, d, J=2.1 Hz) 7.63 (1H, dd, J=8.4 and 2.1 Hz), 7.51 (1H, d, J=8.4 Hz), 2.44, (3H, s); $^{13}$C NMR (100 MHz, DMSO-d6) δ 172.4, 166.0, 158.4, 148.7, 136.1, 134.7, 133.8, 132.7, 130.4, 130.4, 125.5, 124.0, 123.7, 123.7, 121.5, 118.3, 98.5, 20.6; HRMS (ESI): for $C_{17}H_{12}N_3O_4$ calcd: 322.0828; [M+H]. Found: 322.0832.

Keto Nitrile 28

$^1$H NMR (400 MHz, CDCl$_3$) δ 11.89 (1H, s), 9.00 (1H, d, J=8.3 Hz), 7.50 (1H, s), 7.48 (1H, d, J=8.3 Hz), 4.17 (2H, s), 2.41 (3H, s); $^{13}$C NMR (100 MHz, CDCl$_3$) δ 199.3, 191.0, 139.2, 136.7, 135.0, 130.6, 123.5, 122.1, 113.5, 31.2, 21.2, 18.7;

Bicyclic Nitrile 29

$^1$H NMR (400 MHz, DMSO-d6) δ 12.89 (1H, s), 7.85 (1H, s), 7.51 (1H, d, J=8.3 Hz), 7.44 (1H, d, J=8.3 Hz), 2.36 (3H, s); $^{13}$C NMR (100 MHz, DMSO-d6) δ 171.2, 164.9, 138.2, 135.1, 134.7, 123.7, 121.0, 118.1, 116.0, 98.8, 20.8;

Butyryl Amide $^1$H NMR (400 MHz, DMSO-d6) δ 12.93 (1H, s), 10.74 (1H, s), 8.00 (1H, d, J=2.0 Hz), 7.62 (1H, dd, J=8.4 and 2.0 Hz), 7.47 (1H, d, J=8.4 Hz), 2.60 (2H, J=7.4 Hz), 2.42 (3H, s), 1.65 (2H, hex, J=7.4 Hz), 0.95 (3H, t, J=7.4 Hz); $^{13}$C NMR (100 MHz, DMSO-d6) δ 174.2, 171.X, 164.1, 153.3, 138.5, 135.2, 133.2, 124.7, 122.6, 118.1, 109.8, 38.7, 20.7, 18.0, 13.7; HRMS (FAB+): for Receptor Binding Affinity of test substances for the benzodiazepine receptor was determined in vitro by displacement of $^3$H-flumazenil in rat cortical tissue. The results are shown in Table 1.

TABLE 1

$K_i$ Values of novel benzodiazepine analogues tested on $^3$H-Flumazenil binding in vitro rat cortical membranes

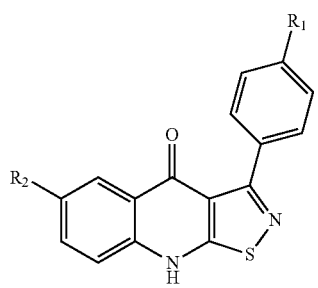

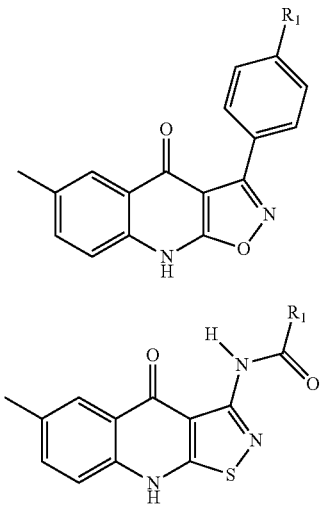

| Compound[b] | $R_1$ | $R_2$ | $K_i$ (nM)[a] |
|---|---|---|---|
| 19 | —Me | —Me | 1.9 |
| 20 | —H | —Me | Not yet Determ. |
| 21 | —Br | —Me | 5.3 |
| 22 | —OMe | —Me | 2.0 |
| 23 | —NO$_2$ | —Me | 5.5 |
| 24 | —Me | —Br | 2.9 |
| 25 | —Me | — | Not yet Determ. |
| 26 | —H | — | 18 |
| 27 | —NO$_2$ | — | Not yet Determ. |
| 31 | —Pr | — | 2.0 |
| 32 | —Et | — | Not yet Determ. |

[a]Each $K_i$ value is the mean of three determinations
[b]The numbering relates to the experimental section above.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the following compounds, their pharmaceutically acceptable salts, hydrates, solvates, optical isomers, and combinations thereof:

Pharmaceutical Composition

The compounds of the present invention may be formulated into conventional pharmaceutical composition comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component, hi tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition. A therapeutically effective amount for the practice of the present invention can be determined by one of ordinary skill in the art using known criteria including the age, weight and response of the individual patient, and interpreted within the context of the disease which is being treated or which is being prevented.

The invention claimed is:

1. A compound selected from the group consisting of the general formulas (I), (II) and (III)

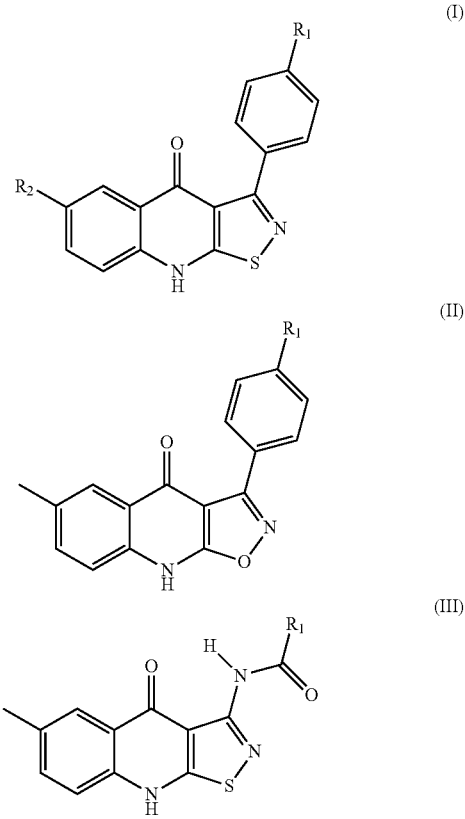

wherein $R_1$ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and $R_2$ is selected from the group consisting of hydrogen, halogen and alkyl having 1 to 2 carbon atoms.

2. The compound according to claim 1, wherein $R_1$ being halogen is selected from the group consisting of bromo and fluoro.

3. The compound according to claim 1, wherein $R_2$ being halogen is selected from the group consisting of bromo and fluoro.

4. The compound according to claim 1, wherein $R_1$ being alkoxy is selected from the group consisting of methoxy and ethoxy.

5. The compound according to claim 1, wherein $R_1$ being alkyl is methyl, ethyl or propyl.

6. The compound according to claim 1, wherein $R_1$ being haloalkyl is trifluoromethyl.

7. The compound according to claim 1, wherein the active compound is selected from the group of
6-Methyl-3-(4-methylphenyl)isothiazoio[5,4-b]quinolin-4(9H)-one (19)
6-Methyl-3-phenylisothiazolo[5,4-b]quinolin-4(9H)-one (20)
3-(4-Bromophenyl)-6-methylisothiazolo[5,4-b]quinolin-4(9H)-one (21)
3-(4-Methoxyphenyl)-6-methylisothiazolo[5,4-b]quinolin-4(9H)-one (22)
6-Methyl-3-(4-nitrophenyl)-isothiazolo[5,4-b]quinolin-4(9H)-one (23)

6-Bromo-3-(4-methylphenyl)isothiazolo[5,4-b]quinolin-4(9H)-one (24)

6-Methyl-3-(4-methylphenyl)isoxazolo[5,4-b]quinolin-4(9H)-one (25)

6-Methyl-3-phenyl-isoxazolo[5,4-b]quinolin-4(9H)-one (26)

6-Methyl-3-(4-nitrophenyl)isoxazolo[5,4-b]quinolin-4(9H)-one (27)

N-(6-methyl-4-oxo-4,9-dihydroisothiazolo[5,4-b]quinolin-3-yl)butanamide N-(6-methyl-4-oxo-4,9-dihydroisothiazolo[5,4-b]quinolin-3-yl)propanamide.

8. Pharmaceutical composition comprising as an active ingredient one or more of the compounds of the general formulas (I), (II) and (III)

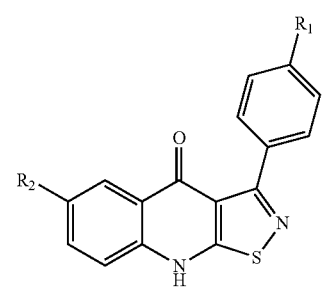

(I)

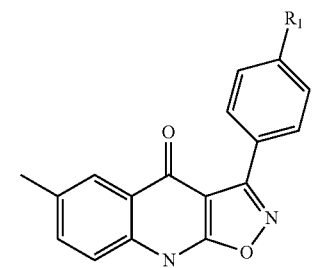

(II)

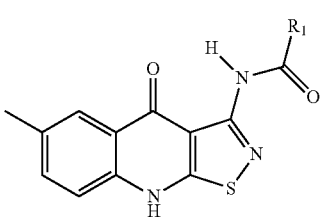

(III)

wherein $R_1$ is selected from the group consisting of hydrogen, halogen, haloalkyl having 1-2 carbon atoms, alkoxy having 1 to 3 carbon atoms in the alkyl chain, alkyl having 1 to 3 carbon atoms, and nitro, and $R_2$ is selected from the group consisting of hydrogen, halogen and alkyl having 1 to 2 carbon atoms in combination with one or more excipients.

9. Pharmaceutical composition according to claim 8, wherein $R_1$ being halogen is selected from the group consisting of bromo and fluoro.

10. Pharmaceutical composition according to claim 8, wherein $R_2$ being halogen is selected from the group consisting of bromo and fluoro.

11. Pharmaceutical composition according to claim 8, wherein $R_1$ being alkoxy is selected from the group consisting of methoxy and ethoxy.

12. Pharmaceutical composition according to claim 8, wherein $R_1$ being alkyl is methyl, ethyl or propyl.

13. Pharmaceutical composition according to claim 8, wherein $R_1$ being haloalkyl is trifluoromethyl.

14. Pharmaceutical composition according to claim 8, wherein the active compound is selected from the group of 6-Methyl-3-(4-methylphenyl)isothiazolo[5,4-b]quinolin-4(9H)-one (19)

6-Methyl-3-phenylisothiazolo[5,4-b]quinolin-4(9H)-one (20)

3-(4-Bromophenyl)-6-methylisothiazolo[5,4-b]quinolin-4(9H)-one (21)

3-(4-Methoxyphenyl)-6-methylisothiazolo[5,4-b]quinolin-4(9H)-one (22)

6-Methyl-3-(4-nitrophenyl)-isothiazolo[5,4-b]quinolin-4(9H)-one (23)

6-Bromo-3-(4-methylphenyisothiazolo[5,4-b]quinolin-4(9H)-one (24)

6-Methyl-3-(4-methylphenyl)isoxazolo[5,4-b]quinolin-4(9H)-one (25)

6-Methyl-3-phenyl-isoxazolo[5,4-b]quinolin-4(9H)-one (26)

6-Methyl-3-(4-nitrophenyl)isoxazolo[5,4-b]quinolin-4(9H)-one (27)

N-(6-methyl-4-oxo-4,9-dihydroisothiazolo[5,4-b]quinolin-3-yl)butanamide

N-(6-methyl-4-oxo-4,9-dihydroisothiazolo[5,4-b]quinolin-3-yl)propanamide.

\* \* \* \* \*